United States Patent [19]

Burdick et al.

[11] Patent Number: 4,880,749
[45] Date of Patent: Nov. 14, 1989

[54] ANALYTICAL ELEMENT AND ITS USE IN A WHOLE BLOOD HEMOGLOBIN ASSAY

[75] Inventors: Brent A. Burdick; Tai-Wing Wu, both of Rochester; David A. Hilborn, Henrietta; Richard W. Spayd, Rochester, all of N.Y.

[73] Assignee: Eastman Kodak Company, Rochester, N.Y.

[21] Appl. No.: 617,453

[22] Filed: Jun. 5, 1984

[51] Int. Cl.$^4$ .................. G01N 21/78; G01N 33/72
[52] U.S. Cl. .......................... 436/66; 422/56; 422/57; 422/58; 435/805; 436/170
[58] Field of Search .................. 422/55–58; 436/66, 169, 170; 435/805

[56] References Cited

U.S. PATENT DOCUMENTS

| 3,546,131 | 12/1970 | Stern et al. |
| 3,992,158 | 11/1976 | Przybylowicz et al. |
| 4,057,394 | 11/1977 | Genshaw |
| 4,258,001 | 3/1981 | Pierce et al. |
| 4,337,222 | 6/1982 | Kitajima et al. |
| 4,340,565 | 7/1982 | Kitajima et al. |
| 4,341,257 | 7/1982 | Zander et al. |
| 4,430,436 | 2/1984 | Koyama ............... 422/56 X |

FOREIGN PATENT DOCUMENTS 2052056 1/1981 United Kingdom.

OTHER PUBLICATIONS

Perutz et al., Biochem., 17, pp. 3640–3652, (1978).
Oshiro et al., Rinsho Byorei, 29(2), pp. 203–209, (1981).
Gersonde, J. Mol. Biol., 42, pp. 285–300, (1969).
Katz et al., Biochem., 12(4), pp. 710–713, (1973).
Gersonde, J. Mol. Biol., 14, pp. 37–47, (1965).

Primary Examiner—Robert J. Hill, Jr.
Attorney, Agent, or Firm—J. Lanny Tucker

[57] ABSTRACT

Disclosed herein is an assay useful for the quantitative determination of hemoglobin in whole blood. This assay utilizes a multizone element comprising a registration zone comprising particulate barium sulfate distributed in a "blush" polymer, and a spreading zone having a void volume and an average pore size (e.g. greater than 5 microns) effective to accommodate whole blood. The element also contains an interactive composition capable of converting substantially all forms of hemoglobin into a detectable end product. One particularly useful interactive composition comprises a hemoglobin oxidizing agent (e.g. ferricyanide) and thiocyanate. Another useful interactive composition comprises an ionic surfactant, e.g. sodium octyl sulfate or sodium dodecyl sulfate.

15 Claims, No Drawings

ANALYTICAL ELEMENT AND ITS USE IN A WHOLE BLOOD HEMOGLOBIN ASSAY

FIELD OF THE INVENTION

The present invention relates to a "dry chemistry" assay for whole blood. In particular, it relates to a dry chemistry assay useful for the quantitative determination of hemoglobin in whole blood. This invention also relates to multizone elements useful in such an assay.

BACKGROUND OF THE INVENTION

Hemoglobin, a protein containing iron in a protoporphyrin IX prosthetic group, functions physiologically as the principal carrier of oxygen in whole blood from the lungs to other body tissues. It is also the protein found in highest concentration in whole blood (normally 12-18 gram percent). Lower than normal values are symptomatic of anemia. Higher than normal values are indicative of polycythemia or erythrocytosis. The determination of hemoglobin content of whole blood is done routinely and, thus, is one of the most frequently performed clinical laboratory tests.

Numerous methods and devices for the determination of hemoglobin are known. Hemoglobin can be assayed *directly*, as in the Tallquist Method, by measuring the transmission or reflection optical density of the red color imparted by oxyhemoglobin (one form of hemoglobin) without any further chemical modification of the hemoglobin. Such "direct" measurement is described, for example, in U.S. Pat. Nos. 4,057,394 (issued Nov. 8, 1977 to Genshaw) and 4,337,222 (issued June 29, 1982 to Kitajima et al).

However, hemoglobin exists in blood in several forms [e.g. oxyhemoglobin ($HbO_2$), deoxyhemoglobin (Hb), methemoglobin (metHb), carboxyhemoglobin (HbCO) and sulfhemoglobin (HbS)], each with a unique absorption spectrum. See, e.g. *Fundamentals to Clinical Chemistry*, N. W. Tietz (Ed.), W. B. Saunders, Co., Philadelphia, 1970, pp. 263-267.

It would be desirable to measure *all* forms of hemoglobin to determine total hemoglobin with a single measurement. This requires the chemical conversion of the various forms of hemoglobin into a single detectable and stable form. Attempts have been made using "indirect" assay methods whereby most forms of hemoglobin are converted to one detectable end product. In one commonly used method, the iron in hemoglobin is oxidized (from $Fe^{+2}$ to $Fe^{+3}$) with a ferricyanide, thus converting the hemoglobin forms to methemoglobin, followed by conversion of the methemoglobin to cyanmethemoglobin with a cyanide. This well known Drabkin's method is fairly rapid and suitable for solution assay. It has been adopted internationally as the approved standard method for hemoglobin measurement (see *J. Clin. Path.*, 31, pp. 139-143 (1978)).

Dry chemistry assays are known. Such assays are analytical techniques wherein chemical reagents are incorporated in various substantially "dry-to-the-touch" elements, e.g. test strips and multizone analytical elements. The advantages of dry chemistry assays over wet chemistry assays (i.e. techniques using reagents in solutions) are also known and include simplicity of use, economic savings and rapid analysis. See, for example, U.S. Pat. No. 3,992,158 (issued Nov. 16, 1976 to Przybylowicz et al).

However, in attempting to adapt the indirect Drabkin method to existing dry chemistry assays, several problems have been encountered. In solution assays, a 250-fold dilution of the blood sample is necessary. However, such dilution is undesirable for automated analyses because it complicates the analyses. Hence, the concentration of hemoglobin would be significantly higher in undiluted dry assays and the small amount of Drabkin's reagent (i.e. cyanide) generally used in diluted solution assays is insufficient to provide an accurate dry assay. To compensate for this deficiency in a dry element, the amount of ferricyanide and cyanide must be significantly increased. However, potassium cyanide, which is commonly used in the Drabkin test, is extremely toxic particularly at the higher concentrations. The danger presented to those who would prepare or use dry analytical elements containing high amounts of potassium cyanide is unacceptable. Hence, it would be desirable to replace this particular reagent while obtaining highly quantitative analyses.

Other agents are known to react with the oxidized forms of hemoglobin. For example, Perutz et al in *Biochem.*, 17, pp. 3640-3652 (1978), describe a study of the reaction of various forms of hemoglobin with thiocyanate. No hemoglobin assay using dry elements is described in this reference.

It has also been observed that some surface active agents (i.e. surfactants) can convert various forms of hemoglobin into detectable products. For example, U.K. patent No. 2,052,056 (published Jan. 21, 1981) describes the use of water-soluble nonionic detergents in alkaline solution to convert hemoglobin and its derivatives to an end product measurable at 575 nm. A similar use of anionic or cationic detergents is particularly discouraged in this reference's teaching. Another reference, namely Oshiro et al, *Rinsho Byorei*, 29(2), pp. 203-209 (1981) describes the use of sodium dodecyl sulfate in a solution assay for hemoglobin.

However, attempts to adapt these known solution assay techniques to dry chemistry assays have not provided acceptable results. Although dry elements for hemoglobin assays have previously been prepared containing a thiocyanate or anionic surfactant reagent, those elements exhibited poor precision, that is, the random error in analytical measurements has been unacceptably high when they were used.

Hence, there is a need in the art for a simple dry chemistry element for rapid determination of hemoglobin in whole blood, which assay avoids toxic reagents, exhibits improved precision and obviates the need to wipe off excess blood.

SUMMARY OF THE INVENTION

The present invention provides a dry chemistry assay useful for determination of hemoglobin in whole blood. This assay overcomes the problems associated with known whole blood assays using dry elements. It is simple, rapid and highly precise and can accommodate either diluted or undiluted whole blood samples, thereby obviating the need to wipe off excess blood. In particular, the elements of this invention exhibit high precision (defined hereinbelow) as well as high sensitivity to the presence of hemoglobin in the test sample. An accurate reading of total hemoglobin is obtained with these embodiments because the reagents used convert substantially all forms of hemoglobin into a single detectable end product.

Therefore, in accordance with this invention, a multizone element for the determination of hemoglobin in whole blood comprises, in order and in fluid contact, a registration zone and a spreading zone. The registration zone comprises particulate barium sulfate distributed in a blush polymer. The spreading zone has a void volume and an average pore size effective to accommodate whole blood. The element also contains an interactive composition capable of converting substantially all forms of hemoglobin into a detectable species. In preferred embodiments, this interactive composition is either the combination of a hemoglobin oxidizing agent and thiocyanate; or an ionic surfactant.

This invention also provides a method for the determination of hemoglobin in whole blood. This method comprises the steps of: (A) physically contacting a sample of whole blood and the multizone element described hereinabove to convert all forms of hemoglobin into a detectable species; and (B) quantitatively detecting that species.

DETAILED DESCRIPTION OF THE INVENTION

The assay of this invention provides a highly accurate analysis of hemoglobin in whole blood. Particularly, it provides an assay having an improved precision, i.e. generally having a lower coefficient of variation than known assays. This means that the random error in analyses is reduced with this invention. Coefficient of variation is defined as $S \div X \times 100\%$, or the standard deviation "S" about a mean X using a number of replicates. The assay of this invention exhibits a desirably low standard deviation of less than about 0.3 g %. Besides improved precision, the present invention provides analytical elements which are highly sensitive to hemoglobin.

The assay of this invention is suitable for analysis of hemoglobin in whole blood, diluted or undiluted. But one of its advantages is its capability for analyzing undiluted whole blood so that the assay is very simple and easily automated. The advantages obtained with the assay of this invention are possible with the use of a multizone element which has two essential zones, a spreading zone which can accommodate, or completely absorb without being saturated, a whole blood sample (e.g. 1–20 μL) without the need to wipe off excess blood, and a registration zone comprised of barium sulfate distributed in a blush polymer (described hereinbelow).

Generally, in order to accommodate an undiluted whole blood sample, the void volume in the spreading zone is in the range of from about 25 to about 80 percent depending upon the materials used, and preferably from about 40 to about 60 percent. The average pore size is generally at least about 5 microns, and more likely is from about 15 to about 65 microns depending upon the materials used.

The spreading zone can be prepared from any suitable fibrous or non-fibrous material or mixtures thereof as long as the zone can accommodate whole blood with the appropriate void volume and average pore size. The spreading zone is advantageously isotropically porous and produces a uniform concentration of whole blood per unit area at its surface facing the registration zone with which the spreading zone is in fluid contact. Such concentration uniformity can be determined by densitometric or other analytical techniques known in the art.

Useful spreading zones having the desired porosity can be prepared using fibrous materials, either mixed with a suitable binder material or woven into a porous fabric, as described in U.S. Pat. No. 4,292,272 (issued Sept. 29, 1981 to Kitajima et al), the disclosure of which is incorporated herein by reference in its entirety. Alternatively, the zones can be prepared using blush polymers according to the teaching of U.S. Pat. No. 3,992,158 (issued Nov. 16, 1976 to Przybylowicz et al), the disclosure of which is incorporated herein by reference in its entirety. Suitable porosity for accomodating whole blood samples can be obtained with appropriate "blushing" conditions.

Isotropically porous spreading zones can also be prepared with particulate material wherein the isotropic porosity is created by interconnected spaces between the particles. Various types of particulate matter, all desirably non-swellable in and chemically inert and impermeable to whole blood components, are useful including, for example, pigments (e.g. titanium dioxide, barium sulfate, etc.), diatomaceous earth, colloidal materials (e.g. microcrystalline cellulose), resinous or glass beads and the like. If a particulate material of choice is not adherent, it can be treated to obtain particles that adhere to each other on surface areas of adjacent particles where those particles are in closest proximity to form a coherent, three-dimensional lattice which is non-swellable in whole blood.

Examples of other useful particulate materials include the polymer particles described in U.S. Pat. No. 4,430,436 (issued Feb. 7, 1984 to Koyama et al), which particles are chemically bonded through reactive groups at the points of particle contact which reactive groups are incorporated in the particles; and the polymer particles described in Japanese patent publication No. 57(1982)-101760 (published June 24, 1982 and assigned to Konishiroku Photo), which particles are chemically bonded at points of contact with a low molecular weight adhesive compound e.g. reaction products of bisphenols, dicarboxylic acids, and/or amino compounds, etc.).

Particularly useful spreading zones are those having a particulate structure formed by organo-polymeric particles and polymeric adhesive for those particles described in U.S. Pat. No. 4,258,001 (issued Mar. 24, 1981 to Pierce et al), the disclosure of which is incorporated herein in its entirety. The interconnected voids among the adjacent particles of such a structure accommodate the corpuscular and high molecular weight components of whole blood and provide for transport of hemoglobin therein. Maintaining particulate integrity of the organopolymeric particles in the particulate structure with a polymeric adhesive prevents the coalescence and flow of these materials into the voids, and the concentration of such adhesive at those particle surface areas of the structure which are contiguous to adjacent particles insures that the adhesive does not flow into and clog the voids.

The materials used to prepare the spreading zone preferred in the practice of this invention are described in considerable detail in the Pierce et al patent. Since the details and definitions of the spreading zone are provided in that reference, the present disclosure is directed to a general description of the zone while noting preferred embodiments of this invention. The thickness of the described particulate structure can be widely varied depending upon the size of the organo-polymeric particles. However, the thickness is generally within the range of from about 10 to about 500 microns.

The heat-stable, organo-polymeric particles useful in the practice of this invention are generally spherical beads having a particle size in the range of from about 1 to about 200 microns. Preferably, they have a particle size within the range of from about 20 to about 80 microns.

The particles can be composed of a wide variety of organic polymers, including both natural and synthetic polymers, having the requisite properties. Preferably, however, they are composed of one or more addition polymers formed from one or more ethylenically unsaturated polymerizable monomers, such as addition homopolymers of single monomers or copolymers formed from two or more of such monomers. These polymers can be prepared by any of a variety of conventional polymerization methods (e.g. solution, emulsion, dispersion, suspension, etc.). If desired, although the invention is not so limited, the particular polymer can contain one or more reaction sites to link various interactive compositions to the particles.

Particularly useful addition polymers are those formed by polymerizing one or more of the following ethylenically unsaturated polymerizable monomers, the details of which are provided in the Pierce et al patent noted hereinabove:

(a) from 0 to 100, preferably from 0 to about 99, weight percent of one or more amino-substituent-free vinyl carbocyclic aromatic monomers, including the styrene monomers described in the Pierce et al patent, as well as similar amino-substituent-free vinyl naphthyl monomers;

(b) from 0 to about 25 weight percent of one or more acrylic acid esters;

(c) from 0 to 100, preferably 0 to about 75, weight percent of one or more methacrylic acid esters;

(d) from 0 to about 30 weight percent of one or more ethylenically unsaturated carboxylic acids;

(e) from 0 to about 75 weight percent of one or more ethylenically unsaturated nitrile;

(f) from 0 to about 20 weight percent of one or more amino-substituted vinyl carbocyclic aromatics, including the styrene monomers described in the Pierce et al patent, as well as similar amino-substituted vinyl naphthyls;

(g) from 0 to about 20, preferably 0 to about 10, weight percent of one or more ethylenically unsaturated crosslinkable monomers, including those which can be crosslinked with amines or gelatin hardeners and those having two or more ethylenically unsaturated polymerizable groups;

(h) from 0 to about 20 weight percent of one or more tertiary aminoalkyl acrylates or methacrylates;

(i) from 0 to 100, preferably 0 to about 75, weight percent of one or more polymerizable, N-heterocyclic vinyl monomers; and (j) from 0 to about 20 weight percent of one or more acrylamides or methacrylamides.

Particularly useful addition polymers include those listed in Table I of the Pierce et al patent. The numbers in the brackets represent the weight ratio of monomers in the monomer blend used to prepare the polymer. Poly(vinyltoluene-co-p-t-butylstyrene-co-methacrylic acid) [61:37:2] is a preferred polymer. The organopolymeric particles can contain other addenda, if desired, as known in the art.

The polymeric adhesive which is useful in this invention bonds the organo-polymeric particles to one another to provide a coherent, three-dimensional lattice in the spreading zone. The details of this adhesive are provided in the Pierce et al patent, noted hereinabove.

Generally, the adhesive is composed of an organic polymer different from the specific polymer contained in the particles, although quite commonly the adhesive represents a polymer containing many repeating units which are identical or similar to some of those present in the polymer composition of the particles.

Preferably, the adhesive is composed of one or more addition polymers formed from one or more ethylenically unsaturated polymerizable monomers, such as addition copolymers formed from two or more of such monomers. Like the particles, the adhesive can be prepared by any of a variety of conventional polymerization methods.

Generally, the amount of adhesive contained in the particulate structure is less than about 10 percent, and preferably from about 1 to about 5 percent, based on the weight of the particles.

Particularly useful addition polymers employed as adhesives are formed by polymerizing a blend of ethylenically unsaturated polymerizable monomers selected from the blends described as follows, the details of which are provided in the Pierce et al patent noted hereinabove:

A. a blend containing from about 1 to about 35, preferably from about 10 to about 30, weight percent of one or more amino-substituent-free vinyl carbocyclic aromatics as described hereinabove, and from about 65 to about 99, preferably from about 70 to about 90, weight percent of one or more alkyl acrylates or methacrylates;

B. a blend containing from about 20 to about 95, preferably from about 50 to about 95, weight percent of one or more amino-substituent-free vinyl carbocyclic aromatics, acrylic or methacrylic acid esters and ethylenically unsaturated polymerizable crosslinkable monomers, and from about 5 to about 80, preferably from about 5 to about 50, weight percent of one or more ethylenically unsaturated polymerizable monomers having an active hydrogen or salts thereof;

C. a blend containing from about 15 to 100 weight percent of one or more ethylenically unsaturated monomers selected from the group consisting of 1-vinylimidazole, vinylbenzyl alcohol, ethyl acrylate or an acrylamide or methacrylamide, and from 0 to about 85 weight percent of one or more ethylenically unsaturated polymerizable crosslinkable monomers; and D. a blend containing from about 80 to about 98, and preferably from about 85 to about 98, weight percent of one or more acrylic or methacrylic acid esters, and from about 2 to about 20 and preferably from about 2 to about 15, weight percent of one or more ethylenically unsaturated polymerizable monomers containing one or more anionic moieties (e.g. carboxy, sulfino, sulfo, phosphono, etc. or alkali metal or ammonium salts thereof).

Particularly useful addition polymers include those listed in Table II of the Pierce et al patent and in U.S. Pat. No. 4,283,491 (issued Aug. 11, 1981 to Dappen), the disclosure of which is incorporated herein by reference. The numbers in the brackets represent the weight ratio of monomers in the monomer blend used to prepare the polymer. Poly(methyl acrylate-co-2-acetoacetoxyethyl methacrylate-co-2-acrylamido-2-methylpropanesulfonic acid) [88:7:5] is a preferred adhesive polymer.

Various methods can be employed for preparing the particulate structure with the above-described particles and adhesive. Specific details of useful methods are provided in the Pierce et al patent noted hereinabove.

The two essential zones of the elements of this invention can be self-supporting (i.e. having enough strength together to have physical integrity), but preferably they are carried on a suitable support. Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include polystyrene, polyesters [e.g. poly(ethylene terephthalate)], polycarbonates, cellulose esters (e.g. cellulose acetate), etc. Preferably, the registration zone is immediately adjacent the support although an optional subbing zone can be interposed, if desired. The zones of the element are in fluid contact with each other, meaning that fluids and reagents and reaction products in the fluids can pass between superposed regions of adjacent zones. Stated in another manner, fluid contact refers to the ability to transport components of a fluid between the zones in fluid contact. Preferably, the zones are separate coated layers, although one or more zones can be in a single coated layer of an element. Conversely, each zone can contain more than one coated layer.

The registration zone of the element is where the detectable species formed by interaction of an interactive composition (described hereinbelow) with hemoglobin is "registered" or detected. This zone contains particulate barium sulfate distributed uniformly throughout a "blush" polymer. The amount of barium sulfate incorporated in the zone can be widely varied, but it is generally from about 50 to about 150, and preferably from about 80 to about 120, $g/m^2$.

The registration zone also comprises a "blush" polymer. Such polymers are generally prepared by dissolving a polymer in a mixture of two liquids, one of which is a lower boiling, good solvent for the polymer and the other of which is a higher boiling, poor solvent for the polymer. Such polymer solution is then coated on a substrate and dried under controlled conditions. The lower boiling solvent evaporates more readily and the coating becomes enriched in the poor solvent. As evaporation proceeds under proper conditions, the polymer becomes isotropically porous (as that term is used in the art) having interconnected pores. The porosity of this zone, however, is less than that of the spreading zone described hereinabove. Generally, the porosity is such that it can not accomodate a sample of whole blood like the spreading zone can. This lower porosity can be obtained with known blushing techniques, and the average pore size is generally less than about 5 microns.

Many different polymers can be used, singly or in combination, for preparing a blush polymer, such as polycarbonates, polyamides, polyurethanes and cellulose esters, with cellulose acetate being preferred. The blush polymer (or mixture thereof) is generally present in the registration zone at a coverage of from about 4 to about 12, and preferably from about 6 to about 10, $g/m^2$. Solvent mixtures useful for preparing blush polymers are well known in the art.

The registration zone can be a single coated layer of the blush polymer containing particulate barium sulfate. Alternatively, the zone can comprise two or more separate coated layers, one or more of which contains the blush polymer. For example, the registration zone can comprise a blush polymer layer, and a gelatin layer or a reagent layer. The interactive composition (described hereinbelow) can be in one or more layers of that zone, if desired, or it can be entirely in the spreading zone.

The elements of this invention can also optionally include additional zones having specialized functions, e.g. making element manufacture more convenient. For example, it is common practice to use additional zones to promote or control adhesion between other zones. Such zones are commonly referred to as "binder" zones or "subbing" zones and are well known in the art. Such subbing zones generally contain one or more naturally-occurring or synthetic polymeric materials including gelatin or other naturally-occurring colloids; or homopolymers and copolymers, such as poly(acrylamide), poly(vinyl pyrrolidone), poly(n-isopropylacrylamide), poly(acrylamide-co-N-vinyl-2-pyrrolidone) and similar copolymers.

The element of this invention also contains an interactive composition. Any hemoglobin oxidative chemistry compatible with the described element format and components can be used in the practice of this invention. However, unlike the Drabkin's reagent known in the art, the interactive compositions particularly useful in the present invention are capable of rapidly converting all forms of hemoglobin (including HbCO) into a single detectable species. The entire interactive composition can be located in either the spreading zone or in the registration zone. Alternatively, individual components of the composition can be in either or other zones. Preferably, all components of the composition are in the spreading zone, thereby making that zone a spreading-/reagent zone.

In one preferred embodiment, the interactive composition consists essentially of one or more ionic surfactants. In other words, an ionic surfactant (or mixture of more than one) is the sole essential component of the composition. A wide variety of ionic surfactants, both anionic and cationic, can be used in the practice of this invention. Anionic surfactants are preferred.

Useful anionic surfactants are alkali metal or ammonium salts of alkanes having from 6 to 20 carbon atoms in the alkyl group, and at least one acidic anionic substituent, such as a sulfate, sulfonate, phosphate, phosphonate, etc. Examples of useful anionic surfactants are sodium octyl sulfate, sodium nonyl sulfate, sodium decyl sulfate, sodium undecyl sulfate, sodium dodecyl sulfate, sodium tridecyl sulfate and sodium tetradecyl sulfate.

Useful cationic surfactants comprise at least one quaternary ammonium cation and an alkyl group having 8 or more carbon atoms. Examples of useful cationic surfactants include decyltrimethylammonium bromide, dodecyltrimethylammonium bromide and dodecyltrimethylammonium chloride.

Sodium dodecyl sulfate and sodium octyl sulfate are the most preferred surfactants in the practice of this invention.

In another preferred embodiment of this invention, the interactive composition comprises a thiocyanate reagent, generally in the form of a salt (e.g. sodium thiocyanate, potassium thiocyanate, etc.). This thiocyanate reagent is used in combination with a hemoglobin oxidizing agent in a modification of the Drabkin's reagent used conventionally for "wet" chemistry hemoglobin determinations. Useful hemoglobin oxidizing agents include a ferricyanide, a nitrite (e.g. sodium nitrite), and others known in the art. The ferricyanide is preferred and is generally present in the form of a salt (e.g. sodium ferricyanide, potassium ferricyanide, etc.). This interactive composition is believed to provide a determination of hemoglobin according to the following equations:

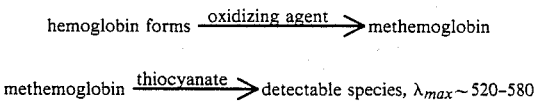

The species obtained with either the anionic surfactant or the thiocyanate reagent can be determined spectrophotometrically, as illustrated in the examples provided hereinbelow.

The coverage of each component or reagent of the interactive compositions described herein can be widely varied. These coverages are generally as follows: the ionic surfactant, when used, is generally present in a coverage of up to about 15, and preferably from about 5 to about 12 g/m$^2$; the hemoglobin oxidizing agent, when used, is generally present in a coverage of up to about 8, and preferably from about 1 to about 4 g/m$^2$; and the thiocyanate ion, when used, is generally present in a coverage of up to about 8, and preferably from about 1 to about 4 g/m$^2$.

One or more zones (or layers) of the elements of this invention can contain a variety of other desirable components, including surfactants, thickeners, buffers (e.g. for pH between about 5 and about 9), binders, hardeners, etc. as known in the art. These components can be present in amounts known to one skilled in the art. The elements of this invention can be configured in a variety of forms, including elongated tapes of any desired width, sheets or smaller chips.

The assay of this invention can be manual or automated. In general, the amount of hemoglobin in whole blood is determined by taking the element from a supply roll, chip packet or other source and physically contacting it with a sample of the whole blood (e.g. 1–20 μL). Such contact can be accomplished in any suitable manner, e.g. dipping or immersing the element into the sample or, preferably, by spotting the spreading zone of the element by hand or machine with a drop of the sample by pipette or other suitable dispensing means.

After sample application, the element is exposed to any conditioning, such as incubation, heating or the like, that may be desirable to quicken or otherwise facilitate obtaining the test result.

Hemoglobin, if present, then interacts with the interactive composition and the hemoglobin concentration in the sample can be determined as directly proportional to the formation of the detectable species. The amount of this species is determined by passing the element through a zone in which suitable apparatus for detecting the species is provided. For example, the species can be detected with suitable spectrophotometric apparatus and procedures known in the art.

The following examples are provided to illustrate the practice of the present invention. In these examples, the polyurethane resin Estane TM was obtained from B. F. Goodrich Chemical Co. (Cleveland, Ohio); Zonyl FSN TM surfactant was obtained from DuPont (Wilmington, Del.); and Triton X-100 TM surfactant was purchased from Rohm & Haas (Philadelphia, Pa). All other reagents and materials were obtained from Eastman Organic Chemicals (Rochester, N.Y.). Whole blood samples were obtained from a local laboratory. Reference hemoglobin levels were determined by that laboratory using a Coulter Hemoglobinometer (available from Coulter Diagnostics, Inc., Hialeah, Fla.) using the procedure described in U.S. Pat. No. 3,874,852 (issued Apr. 1, 1975 to Hamill).

EXAMPLE 1

Hemoglobin Element Using Thiocyanate in the Interactive Composition and a Comparison to Prior Art Elements This example compares an element of this invention for determining hemoglobin to prior art hemoglobin elements.

An analytical element of this invention was prepared by coating a blush polymer mixture of cellulose acetate and polyurethane containing particulate barium sulfate distributed therein to form a registration layer on a poly(ethylene terephthalate) film support. Over the registration layer was coated a polymeric bead spreading/reagent layer. The element format and components are illustrated as follows:

| Spreading/Reagent Layer | |
|---|---|
| Particulate structure comprising: 20–80μ poly(vinyltoluene-co-p-t-butylstyrene-co-methacrylic acid) [61:37:2 weight ratio] and an adhesive of | 100–300 g/m$^2$ |
| poly(methyl acrylate-co-2-acetoacetoxyethyl methacrylate-co-2-acrylamido-2-methylpropanesulfonic acid) [88:7:5 weight ratio] | 2–10 g/m$^2$ |
| Triton X-100 TM surfactant | 0.5–5 g/m$^2$ |
| Potassium phosphate buffer (pH = 7) | 0.5–5 g/m$^2$ |
| Potassium ferricyanide | 1–4 g/m$^2$ |
| Potassium thiocyanate | 1–4 g/m$^2$ |
| Registration Layer | |
| Cellulose acetate | 6–10 g/m$^2$ |
| Polyurethane | 0.5–2 g/m$^2$ |
| Barium sulfate | 80–120 g/m$^2$ |
| Triton X-100 TM surfactant | 0.5–5 g/m$^2$ |
| Support | |

Control A

| Spreading/Reagent Layer | |
|---|---|
| Particulate stucture comprising: 20–80μ poly(vinyltoluene-co-p-t-butylstyrene-co-methacrylic acid) [61:37:2 weight ratio] and an adhesive of | 100–300 g/m$^2$ |
| poly(methyl acrylate-co-2-acetoacetoxyethyl methacrylate-co-2-acrylamido-2-methylpropanesulfonic acid) [88:7:5 weight ratio] | 2–10 g/m$^2$ |
| Triton X-100 TM surfactant | 0.5–5 g/m$^2$ |
| Potassium phosphate buffer (pH = 7) | 0.5–5 g/m$^2$ |
| Zonyl FSN TM surfactant | 0.1–0.5 g/m$^2$ |
| Potassium ferricyanide | 1–4 g/m$^2$ |
| Potassium thiocyanate | 1–4 g/m$^2$ |
| Support | |

Control B

This element was like Control A except Triton X-100 TM was present in a coverage of 0.1–1 g/m$^2$ and sodium dodecyl sulfate (4–15 g/m$^2$) was included as reagent in place of the ferricyanide and thiocyanate.

Control C

This element was like Control A except that titanium dioxide (5–20 g/m$^2$) was also included in the spreading/reagent layer.

Control D

This element was like Control A except that barium sulfate (5–20 g/m²) was also included in the spreading-/reagent layer.

Control E is as illustrated below:

| Control E | |
|---|---|
| Spreading/Reagent Layer | |
| Particulate structure comprising: 20–80μ poly(vinyltoluene-co-p-t-butylstyrene-co-methacrylic acid) [61:37:2 weight ratio] | 100–300 g/m² |
| and an adhesive of poly(methyl acrylate-co-2-aceto-acetoxyethyl methacrylate-co-2-acrylamido-2-methylpropanesulfonic acid) [88:7:5 weight ratio] | 2–10 g/m² |
| Triton X-100 TM surfactant | 0.5–5 g/m² |
| Potassium phosphate buffer (pH = 7) | 0.5–5 g/m² |
| Zonyl FSN TM surfactant | 0.1–0.5 g/m² |
| Dodecyltrimethylammonium bromide surfactant/reagent | 5–12 g/m² |
| Registration Layer | |
| Cellulose acetate | 6–10 g/m² |
| Polyurethane | 0.5–2 g/m² |
| Triton X-100 TM surfactant | 0.5–5 g/m² |
| Titanium dioxide | 80–120 g/m² |
| Support | |

Control F

This element was like Control E except that sodium dodecyl sulfate (5–12 g/m²) was included in place of dodecyltrimethylammonium bromide.

Five samples of each element were tested by applying 7–10μL samples of undiluted whole blood containing various concentrations of hemoglobin (0–20 g %) to the spreading layer of each. Reflectance spectra were measured at 540 nm on a conventional spectrophotometer at room temperature, at 1–5 minutes after sample-element contact. Standard calibration curves were prepared for each element using reference assays. The precision of each element was then determined by calculating the standard deviation of each hemoglobin sample measurement and pooling those standard deviations by usual statistical calculations. Acceptable values for the pooled standard deviations are less than about 0.3 gram percent (hemoglobin concentration). Table I below presents the precision data for the tested elements. Example 1 (the element of this invention) and Control F exhibited acceptable precision. However, Control F was very difficult to prepare, showed very poor sensitivity to the presence of hemoglobin in the test sample, and exhibited a very slow spread time when the element was spotted with the test sample. Hence, Control F would not be a suitable element for commercialization. Example 1, in contrast, exhibited desired precision, sensitivity to hemoglobin and rapid spreading time suitable for commercialization, and was easily prepared.

TABLE I

| Element | Precision (g %) |
|---|---|
| Example 1 | 0.30 |
| Control A | 0.70 |
| Control B | 0.86 |
| Control C | 0.68 |
| Control D | 0.70 |
| Control E | 0.53 |
| Control F | 0.25 |

EXAMPLE 2

Hemoglobin Assay Using an Anionic Surfactant as the Interactive Composition

An analytical element was prepared similar to that of Example 1 except that sodium dodecyl sulfate (5–12 g/m²) was used in place of the thiocyanate and ferricyanide reagents in the spreading layer, and Triton X-405 TM (available from Rohm & Haas, Philadelphia, Pa.) (0.5–5 g/m²) was used in place of Triton X-100 TM in the registration layer.

This element was evaluated according to the procedure described in Example 1, and its precision was determined to be 0.20 g %.

EXAMPLE 3

Hemoglobin Assay with the Reagents in the Registration Zone

An element for determining hemoglobin in whole blood was prepared having the format and components shown below coated on a poly(ethylene terephthalate) support. The registration zone contained two separate coated layers. Samples of this element were tested by the procedure described in Example 1. The precision was determined to be 0.2 g %.

| | | | |
|---|---|---|---|
| Spreading Layer | Particle structure comprising: 20–80μ poly(vinyltoluene-co-p-t-butylstyrene-co-methacrylic acid) [61:37:2 weight ratio] and an adhesive of poly(methyl acrylate-co-2-aceto-acetoxyethyl methacrylate-co-2-acrylamido-2-methylpropanesulfonic acid) [88:7:5 weight ratio] | | 100–300 g/m² |
| | | | 2–10 g/m² |
| | Zonyl FSN TM surfactant | | 0.1–0.5 g/m² |
| Registration Zone | Blush Polymer Layer | Cellulose acetate | 6–10 g/m² |
| | | Polyurethane | 0.5–2 g/m² |
| | | Barium sulfate | 80–120 g/m² |
| | | Triton X-100 TM surfactant | 0.5–5 g/m² |
| | Reagent Layer | Gelatin (hardener) | 5–15 g/m² |
| | | Zonyl FSN TM surfactant | 0.1–0.5 g/m² |
| | | Potassium phosphate buffer (pH 7) | 0.5–5 g/m² |
| | | Potassium ferricyanide | 1–4 g/m² |
| | | Potassium thiocyanate | 1–4 g/m² |
| Support | | | |

EXAMPLE 4

Hemoglobin Assay Having the Reagents in the Spreading Layer

An element for determining hemoglobin in whole blood was prepared having the format and components shown below coated on a poly(ethylene terephthalate) support. The registration zone contained two separate coated layers. However, the reagents which interact with hemoglobin were placed in the spreading layer making it a spreading/reagent layer. Samples of this element were tested by the procedure described in Example 1. The precision was determined to be 0.1 g %.

| | |
|---|---|
| Particulate structure comprising: 20–80μ poly(vinyltoluene-co-p-t-butylstyrene-co-methacrylic acid) [61:37:2 weight ratio] | 100–300 g/m² |

| | -continued | | |
|---|---|---|---|
| Spreading/Reagent Layer | and an adhesive of poly(methyl acrylate-co-2-acetoacetoxyethyl methacrylate-co-2-acrylamido-2-methylpropanesulfonic acid) [88:7:5 weight ratio] | 2-10 g/m² | |
| | Triton X-100 TM surfactant | 2-4 g/m² | |
| | Potassium phosphate buffer (pH 7) | 0.5-5 g/m² | |
| | Potassium ferricyanide | 1-4 g/m² | |
| | Potassium thiocyante | 1-4 g/m² | |
| Blush Polymer Layer | Cellulose acetate | 6-10 g/m² | |
| | Polyurethane | 0.5-2 g/m² | |
| | Barium sulfate | 80-120 g/m² | |
| Registration Zone | Triton X-100 TM surfactant | 0.5-5 g/m² | |
| Gelatin Layer | Gelatin (hardener) | 5-20 g/m² | |
| | Poly(methyl acrylate-co-2-acetoacetoxyethyl methacrylate-co-2-acrylamido-2-methylpropanesulfonic acid) [88:7:5 weight ratio] | 5-20 g/m² | |
| | Alkanol XC TM surfactant | 0.1-1 g/m² | |
| | Potassium phosphate buffer (pH 7) | 0.5-5 g/m² | |
| Support | | | |

The invention has been described in detail with particular reference to preferred embodiments thereof, but it will be understood that variations and modifications can be effected within the spirit and scope of the invention.

We claim:

1. A multizone element for the determination of hemoglobin in whole blood, said element comprising, in order and in fluid contact, a registration zone comprising particulate barium sulfate distributed in a blush polymer, and a spreading zone having a void volume of from about 25 to about 80 percent and an average pore size of at least about 5 microns, said spreading zone comprising a particulate structure comprising a plurality of particles non-swellable in and impermeable to whole blood, said particles having a particles size of from about 1 to about 200 microns and being bonded on surface areas of adjacent particles where said adjacent particles are in closest proximity to form a coherent, three-dimensional lattice which is non-swellable in whole blood, said element also containing an interactive composition capable of converting substantially all forms of hemoglobin into a detectable species, said interactive composition consisting essentially of either an ionic surfactant present at a coverage of from about 5 to about 12 g/m², or the combination of a hemoglobin oxidizing agent and thiocyanate.

2. The element of claim 1 wherein said particles are chemically bonded through reactive groups which are incorporated in said particles.

3. The element of claim 1 wherein said particles are bonded with an adhesive material.

4. The element of claim 1 wherein said surfactant is anionic.

5. The element of claim 1 wherein said interactive composition comprises ferricyanide and a thiocyanate.

6. A multizone element for the determination of hemoglobin in whole blood, said element comprising a support having thereon, in order and in fluid contact, a registration zone comprising particulate barium sulfate distributed in a blush polymer, and a spreading zone comprising a particulate structure having a void volume of from about 40 to about 60 percent and an average pore size of at least about 5 microns, said particulate structure comprising:

(i) a plurality of heat-stable, organopolymeric particles non-swellable in an impermeable to whole blood, said particles having a particle size of from about 1 to about 200 microns, and (ii) an adhesive, in an amount less than about 10 percent by weight of said particles, comprising an organic polymer different from that of said particles and insoluble in whole blood;

substantially all of said adhesive being concentrated on surface areas of adjacent particles where said adjacent particles are in closest proximity, and bonding said particles into a coherent, three-dimensional lattice which is non-swellable in whole blood, said element also containing an interactive composition capable of converting substantially all forms of hemoglobin into a detectable species, said interactive composition consisting essentially of an ionic surfactant present at a coverage of from about 5 to about 12 g/m², or the combination of a hemoglobin oxidizing agent and thiocyanate.

7. The element of claim 6 wherein said particles comprise an addition polymer formed from one or more of the following ethylenically unsaturated polymerizable monomers:

(a) up to 100 weight percent of an amino-substituent-free vinyl carbocyclic aromatic;

(b) up to about 25 weight percent of an acrylic acid ester;

(c) up to 100 weight percent of a methacrylic acid ester;

(d) up to about 30 weight percent of an ethylenically unsaturated carboxylic acid;

(e) up to about 75 weight percent of an ethylenically unsaturated nitrile;

(f) up to about 20 weight percent of an amino-substituted vinyl carbocyclic aromatic;

(g) up to about 20 weight percent of an ethylenically unsaturated crosslinkable monomer;

(h) up to about 20 weight percent of a tertiary aminoalkyl acrylate or methacrylate;

(i) up to 100 weight percent of a N-heterocyclic vinyl monomer; and (j) up to about 20 weight percent of an acrylamide or methacrylamide, and said adhesive comprises an addition polymer formed from a blend of ethylenically unsaturated polymerizable monomers selected from the following group:

A. a blend containing from about 1 to about 35 weight percent of one or more amino-substituent-free vinyl carbocyclic aromatics and from about 65 to about 99 weight percent of one or more alkyl acrylates or methacrylates;

B. a blend containing from about 20 to about 95 weight percent of one or more amino-substituent-free vinyl carbocyclic aromatics, acrylic or methacrylic acid esters and ethylenically unsaturated polymerizable crosslinkable monomers, and from about 5 to about 80 weight percent of one or more ethylenically unsaturated polymerizable monomers having an active hydrogen or salts thereof;

C. a blend containing from about 15 to 100 weight percent of one or more ethylenically unsaturated monomers selected from the group consisting of 1-vinylimidazole, vinylbenzyl alcohol, ethyl acrylate or an acrylamide or methacrylamide, and up to 85 weight percent of one or more ethylenically unsaturated polymerizable crosslinkable monomers; and D. a blend containing from about 80 to about 98, and preferably from about 85 to about 98, weight percent of one or more acrylic or methacrylic acid esters, and from about 2 to about 20, and preferably from about 2 to about 15, weight percent of one or more ethylenically unsaturated polymerizable monomers containing one or more anionic moieties.

8. The element of claim 6 wherein said spreading zone has an average pore size of from about 15 to about 65 microns.

9. A multilayer element for the determination of hemoglobin in undiluted whole blood, said element comprising a support having thereon, in order and in fluid contact, a registration layer comprising particulate barium sulfate distributed in a cellulose acetate blush polymer, and a spreading/reagent layer having a void volume and an average pore size effective to accommodate undiluted whole blood and containing ferricyanide and thiocyanate, said spreading/reagent layer comprising a particulate structure comprised of:
(i) a plurality of poly(vinyltoluene-co-p-t-butylstyrene-co-methacrylic acid) (61:37:2 weight ratio) particles having a substantially uniform particle size of from about 20 to about 80 microns; and
(ii) an adhesive, in an amount less than about 10 percent by weight of said particles, comprising poly(methyl acrylate-co-2-acetoacetoxyethyl methacrylate-co-2-acrylamido-2-methylpropane-sulfonic acid) (88:7:5 weight ratio).

10. A multilayer element for the determination of hemoglobin in undiluted whole blood, said element comprising a support having thereon, in order and in fluid contact, a registration layer comprising particulate barium sulfate distributed in a cellulose acetate blush polymer, and a spreading/reagent layer having a void volume and an average pore size effective to accommodate undiluted whole blood and containing an interactive composition consisting essentially of sodium octyl sulfate or sodium dodecyl sulfate surfactant present at a coverage of from about 5 to about 12 g/m$^2$, said spreading/reagent layer comprising a particulate structure comprised of:
(i) a plurality of poly(vinyltoluene-co-p-t-butylstyrene-co-methacrylic acid) (61:37:2 weight ratio) particles having a substantially uniform particle size of from about 20 to about 80 microns; and
(ii) an adhesive, in an amount less than about 10 percent by weight of said particles, comprising poly(methyl acrylate-co-2-acetoacetoxyethyl methacrylate-co-2-acrylamide-2-methylpropane-sulfonic acid) (88:7:5 weight ratio).

11. A method for the determination of hemoglobin in whole blood, said method comprising the steps of:
(A) physically contacting a sample of whole blood and a multizone element, said element comprising, in order and in fluid contact, a registration zone comprising particulate barium sulfate distributed in a blush polymer, and a spreading zone having a void volume of from about 25 to about 80 percent and an average pore size of at least about 5 microns, said spreading zone comprising a particulate structure comprising a plurality of particles non-swellable in and impermeable to whole blood, said particles having a particle size of from about 1 to about 200 microns and being bonded on surface areas of adjacent particles where said adjacent particles are in closest proximity to form a coherent, three dimensional lattice whch is non-swellable in whole blood, said element also containing an interactive composition capable of converting substantially all forms of hemoglobin into a detectable species, said interactive composition consisting essentially of an ionic surfactant present at a coverage of from about 5 to about 12 g/m$^2$, or the combination of a hemoglobin oxidizing agent and thiocyanate; and
(B) quantitatively detecting said detectable species.

12. The method of claim 11 wherein said sample of whole blood is undiluted.

13. The method of claim 11 wherein said particles are bonded with an adhesive, in an amount less than about 10 percent by weight of said particles, comprising an organic polymer different from that of said particles and insoluble in whole blood.

14. The method of claim 11 wherein said detectable species has an absorption $\lambda_{max}$ in the range of from about 520 to about 580 nm.

15. The method of claim 11 wherein said particles comprise an addition polymer formed from one or more of the following ethylenically unsaturated polymerizable monomers:
(a) up to 100 weight percent of an amino-substituent-free vinyl carbocyclic aromatic;
(b) up to about 25 weight percent of an acrylic acid ester;
(c) up to 100 weight percent of a methacrylic acid ester;
(d) up to about 30 weight percent of an ethylenically unsaturated carboxylic acid;
(e) up to about 75 weight percent of an ethylenically unsaturated nitrile;
(f) up to about 20 weight percent of an amino-substituted vinyl carbocyclic aromatic;
(g) up to about 20 weight percent of an ethylenically unsaturated crosslinkable monomer;
(h) up to about 20 weight percent of a tertiary aminoalkyl acrylate or methacrylate;
(i) up to 100 weight percent of a N-heterocyclic vinyl monomer; and
(j) up to about 20 weight percent of an acrylamide or methacrylamide, and said adhesive comprises an addition polymer formed from a blend of ethylenically unsaturated polymerizable monomers selected from the following group:
A. a blend containing from about 1 to about 35 weight percent of one or more amino-substituent-free vinyl carbocyclic aromatics and from about 65 to about 99 weight percent of one or more alkyl acrylates or methacrylates;
B. a blood containing from about 20 to about 95 weight percent of one or more amino-substituent-free vinyl carbocyclic aromatics, acrylic or methacrylic acid esters and ethylenically unsaturated polymerizable crosslinkable monomers, and from about 5 to about 80 weight percent of one or more ethylenically unsaturated polymerizable monomers having an active hydrogen or salts thereof;

C. a blend containing from about 15 to 100 weight percent of one or more ethylenically unsaturated monomers selected from the group consisting of 1-vinylimidazole, vinylbenzyl alcohol, ethyl acrylate or an acrylamide or methacrylamide, and up to 85 weight percent of one or more ethylenically unsaturated polymerizable crosslinkable monomers; and D. a blend containing from about 80 to about 98, and preferably from about 85 to about 98, weight percent of one or more acrylic or methacrylic acid esters, and from about 2 to about 20, and preferably from about 2 to about 15, weight percent of one or more ethylenically unsaturated polymerizable monomers containing one or more anionic moieties.

* * * * *

UNITED STATES PATENT AND TRADEMARK OFFICE
CERTIFICATE OF CORRECTION

PATENT NO. : 4,880,749
DATED : November 14, 1989
INVENTOR(S) : Brent A. Burdick et al It is certified that error appears in the above-identified patent and that said Letters Patent is hereby corrected as shown below:

Col. 14, line 6, delete "an" and substitute therefor --and--.

Col. 15, line 31, delete "-co-p-t-" and substitute therefor -- -co-p-t- --; line 32, delete "-co-" and substitute therefor -- -co- --; line 37, delete "-co-" and substitute therefor -- -co- --; line 38, delete "-co-" and substitute therefor -- -co- --; line 53, delete "-co-p-t-" and substitute therefor -- -co-p-t- --; line 54, delete "-co-" and substitute therefor -- -co- --.

Col. 16, line 10, delete "whch" and substitute therefor --which--; line 63, delete "blood" and substitute therefor --blend--.

Signed and Sealed this

Seventh Day of January, 1992

Attest:

HARRY F. MANBECK, JR.

*Attesting Officer*   Commissioner of Patents and Trademarks